United States Patent
Laffitte

(10) Patent No.: US 11,359,163 B2
(45) Date of Patent: Jun. 14, 2022

(54) USE OF HYPOPHOSPHOROUS ACID FOR THE ESTERIFICATION OF FREE FATTY ACIDS

(71) Applicant: Arkema France, Colombes (FR)

(72) Inventor: Jean-Alex Laffitte, Pau (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/048,409

(22) PCT Filed: Apr. 19, 2019

(86) PCT No.: PCT/FR2019/050937
§ 371 (c)(1),
(2) Date: Oct. 16, 2020

(87) PCT Pub. No.: WO2019/202276
PCT Pub. Date: Oct. 24, 2019

(65) Prior Publication Data
US 2021/0155870 A1    May 27, 2021

(30) Foreign Application Priority Data

Apr. 20, 2018  (FR) ...................... 1853514

(51) Int. Cl.
| | | |
|---|---|---|
| *C11C 3/00* | (2006.01) | |
| *C10L 1/02* | (2006.01) | |
| *C11C 3/10* | (2006.01) | |
| *C07C 309/03* | (2006.01) | |
| *B01J 31/02* | (2006.01) | |

(52) U.S. Cl.
CPC .......... *C11C 3/003* (2013.01); *B01J 31/0257* (2013.01); *C07C 309/03* (2013.01); *C10L 1/02* (2013.01); *C11C 3/10* (2013.01); *C10L 2200/0476* (2013.01)

(58) Field of Classification Search
CPC ... C11C 3/003; C11C 3/10; C10L 1/02; C10L 2200/0476; B01J 31/0257; C07C 309/03
See application file for complete search history.

(56) References Cited

U.S. PATENT DOCUMENTS

| | | | | |
|---|---|---|---|---|
| 3,071,604 A | * | 1/1963 | Mohan | ...................... C11C 3/02 554/170 |
| 3,630,790 A | * | 12/1971 | Schmidt | .................. C23C 22/03 148/248 |
| 3,887,488 A | * | 6/1975 | Scott | ...................... C23F 11/04 252/389.2 |
| 4,695,411 A | | 9/1987 | Stern et al. | |
| 2003/0167681 A1 | | 9/2003 | Delgado Puche | |
| 2007/0149803 A1 | | 6/2007 | Glos et al. | |

FOREIGN PATENT DOCUMENTS

| | | | | |
|---|---|---|---|---|
| CN | 105254686 A | * | 1/2016 | ............... C07H 1/00 |
| EP | 0194165 A | | 9/1986 | |
| FR | 2929621 A1 | | 10/2009 | |
| GB | 979673 A | * | 1/1965 | ............. C08G 65/32 |
| WO | 9501331 A1 | | 1/1995 | |
| WO | 2006043281 A1 | | 4/2006 | |

OTHER PUBLICATIONS

CN 105254686 A, Sun Yu, et al. , Preparation method of alkyl glycoside, English translation, 8 pages (Year: 2016).*
Gaur, B. et al., Corrosion of metals and alloys in methane sulphonic acid, British Corrosin Journal, vol. 34, No. 1, pp. 63-66 (Year: 1999).*
International Search Report and Written Opinion for International Application No. PCT/FR2019/050937, dated Jun. 21, 2019, 5 pages.

* cited by examiner

*Primary Examiner* — Yate' K Cutliff
(74) *Attorney, Agent, or Firm* — RatnerPrestia

(57) ABSTRACT

The use of hypophosphorous acid as a corrosion inhibitor for esterification reactions of free fatty acids contained in a fatty substance is described, particularly in the presence of an organosulfonic acid. The invention also relates to a method for the esterification of fatty acids.

13 Claims, No Drawings

USE OF HYPOPHOSPHOROUS ACID FOR THE ESTERIFICATION OF FREE FATTY ACIDS

CROSS-REFERENCE TO RELATED APPLICATIONS

This is the national phase of International Application No. PCT/FR2019/050937, filed 19 Apr. 2019, which claims priority to French Application No. 1853514, filed 20 Apr. 2018. The disclosure of each of these applications is incorporated herein by reference in its entirety for all purposes.

FIELD OF THE INVENTION

The present invention relates to the esterification reactions of free fatty acids present in various types of oil and fat, whether they be of vegetable, animal or mineral origin.

Another object of the present invention is a method for esterification of free fatty acids present in oils, in particular before transformation of said oils into biofuel, in particular biodiesel.

BACKGROUND OF THE INVENTION

The increase in the cost of fossil raw materials and the development of environment standards now make it necessary to seek new sources of raw materials. Among these new sources, biomass constitutes an alternative of choice, and vegetable, of even animal, oils are already currently being used for manufacturing substances useful in the cosmetic or lubricant field or as raw materials for producing biofuel, in particular biodiesel.

Biodiesel consists for the most part of fatty acid methyl esters. It is generally produced by transesterification of vegetable or animal oils with methanol, in the presence of alkaline catalysts and in particular sodium methylate (NaOMe), potassium methylate (KOMe), sodium hydroxide (NaOH), potassium hydroxide (KOH) or calcium hydroxide (Ca(OH)$_2$).

The transesterification reaction can be shown diagrammatically as follows:

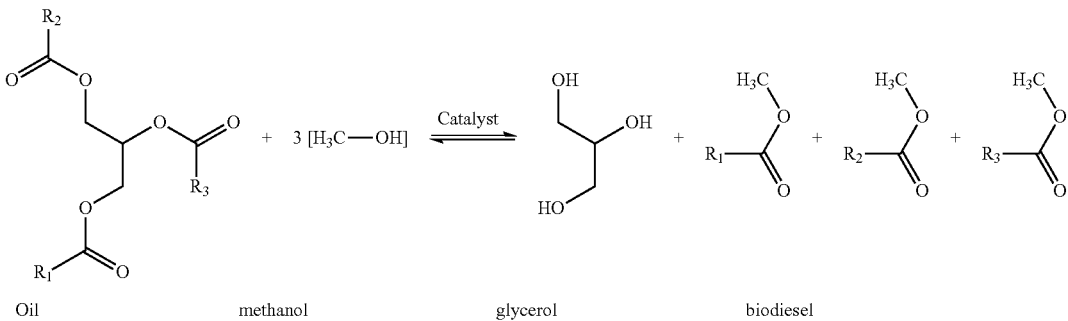

Oil          methanol          glycerol          biodiesel

Biodiesel is this mixture of fatty acid methyl esters.

However, transesterification of oils does pose problems, in particular because of the free fatty acids present in said oils in a quantity that may vary within very great proportions according to the actual origin of the oils. Quantities ranging up to 40% or even 70% free fatty acids have been observed, in particular in certain recycled oils.

However, as from a free fatty acid content in an oil greater than 5%, or even greater than 10%, said free acids react with the basic transesterification catalyst in order to form soaps (fatty acid alkaline or alkaline-earth salts). These soaps may generate emulsions and make it difficult or even impossible to separate glycerol from biodiesel.

In order to avoid the formation of emulsions and soaps, and to optimise the separation of glycerol in the end product, the proportion of free fatty acids before transesterification should be as low as possible, in particular less than 0.5% by weight, advantageously less than 0.1% by weight. This proportion should again preferably be a few ppm, and ideally the free fatty acid content in the oil before transesterification should be zero.

At the present time, free fatty acids are typically esterified with methanol, in the presence of an acid catalyst. The scientific literature and patent literature propose a very great variety of acid catalysts with very great disparities in results concerning the pretreatment of the oils before reducing or even making zero the proportion of free fatty acids before the transesterification reaction leading to biodiesel.

The acid catalysts most commonly used at the present time are sulfuric acid (H$_2$SO$_4$) and p-toluenesulfonic acid (PTSA), and numerous scientific articles and patent application publications disclose studies on esterifications of pre-fatty acids present in vegetable or animal oils or fats.

The use of sulfuric acid nevertheless poses major problems of corrosion and effluents to be treated. As for p-toluenesulfonic acid, this by nature contains an aromatic ring, and may furthermore contain aromatic impurities, which makes it incompatible with environmental standards relating to fuels, which must precisely contain as small a quantity as possible, or even nil, of aromatic compounds.

Methane sulfonic acid (MSA, or the anhydrous form thereof, AMSA, standing for anhydrous methane sulfonic acid) is also often proposed as a catalyst for esterification of free fatty acids. A method for esterification of free fatty acids using MSA as an acid catalyst under operating conditions that are easily transposable to the industrial scale is known from the application FR 2 929 621. This document also discloses the preparation of effective and profitable biofuels.

However, despite the advantages that this method has, it turns out that the esterification of free fatty acids with methanol in the presence of MSA as catalyst causes corrosion vis-à-vis stainless steel at 70° C.

In the case of a glycerolysis reaction, which consists of the esterification of free fatty acids with glycerol, conducted at 120-130° C., the rate of corrosion may be as much as approximately 600 μm/year at 130° C. with MSA.

It has been found that the presence of the acid catalyst for this esterification reaction causes a corrosion of the stainless steel, the material of the reactors used. However, if the reaction is carried out in the absence of acid, in order to limit corrosion, the esterification reaction must be carried out at 220° C., which leads to a much greater energy consumption.

The aforementioned prior art shows clearly that at the present time there does not exist any method allowing the esterification of fatty acids contained in vegetable or animal oils or fats with good yields and which does not cause corrosion vis-à-vis stainless-steel containers.

Moreover, esterifying fatty acids in the presence of hypophosphorous acid for a very different purpose from that sought, namely the improvement and stability of the colour of the esters obtained, is known from the document U.S. Pat. No. 3,071,604.

In a context that is different again, incorporating a phosphorus derivative in order to inhibit the corrosion of stainless steel in an aqueous solution of sulfuric acid is known from the document U.S. Pat. No. 3,887,488.

SUMMARY OF THE INVENTION

Thus, a first objective of the present invention consists of providing a corrosion inhibiter that can be used for methods for the esterification of free fatty acids.

Another objective is to provide an esterification method that uses an acid catalyst causing only little or no corrosion of the esterification plant and able to lead to the production of biofuel with low proportions of aromatic compounds and sulfuretted compounds.

Yet other objectives will appear in the light of the disclosure of the invention that follows.

DETAILED DESCRIPTION OF THE INVENTION

It has in fact been discovered that the use of hypophosphorous acid for reactions of esterification of free fatty acids present in various types of oil and fat, whether they be of vegetable, animal or mineral origin, has the advantage of considerably limiting the corrosion of the stainless-steel equipment.

The expressions "lying between . . . and . . ." and "ranging from . . . to . . ." used in the text of the present description and claims must be understood as each including the bounds mentioned.

Use

Thus, according to a first aspect, the present invention relates to the use of hypophosphorous acid as a corrosion inhibiter for esterification reactions of free fatty acids present in various types of oil or fat, whether they be of vegetable, animal or mineral origin, in the presence of organosulfonic acid.

Hypophosphorous acid has the formula $H_3PO_2$.

The hypophosphorous acid used may be in anhydrous form, that is to say with a 100% hypophosphorous acid content, or in 50% aqueous solution.

In the present invention, organosulfonic acid preferentially means organosulfonic acids of formula $R-SO_3H$, wherein R represents a saturated hydrocarbon chain, linear or branched, including 1 to 4 carbon atoms, or an aryl radical, optionally substituted by a saturated hydrocarbon chain, linear or branched, including 1 to 4 carbon atoms, and optionally substituted, in whole or in part, by one or more halogen atoms, identical or different.

The saturated hydrocarbon chain, linear or branched, including 1 to 4 carbon atoms can be substituted, in whole or in part, by one or more halogen atoms chosen from fluorine, chlorine and bromine, and in particular the hydrocarbon chain may be perhalogenated, more particularly perfluorinated.

"Aryl" means an aromatic radical, preferably phenyl or naphthyl, more preferentially phenyl.

Thus, and non-limitatively, the organosulfonic acids included in the context of the present invention are preferably chosen from methanesulfonic acid, ethanesulfonic acid, n-propanesulfonic acid, iso-propanesulfonic acid, n-butanesulfonic acid, iso-butanesulfonic acid, sec-butanesulfonic acid, tert-butanesulfonic acid, trifluoromethanesulfonic acid, p-toluenesulfonic acid, benzenesulfonic acid and mixtures of two or more thereof, in any proportions.

According to a particularly preferred embodiment, the organosulfonic acid used in the context of the present invention is chosen from methanesulfonic acid, ethanesulfonic acid, trifluoromethanesulfonic acid and p-toluenesulfonic acid and mixtures thereof. Entirely preferably, the acid used is methanesulfonic acid or p-toluenesulfonic acid, and more particularly methanesulfonic acid.

The methanesulfonic acid used may be in anhydrous form, that is to say 100% methanesulfonic acid, also known as AMSA, standing for anhydrous methanesulfonic acid, or in the form of an aqueous solution, for example in the form of a 70% by weight solution in water, sold by the company Arkema.

The reagents of the esterification reaction, namely the fatty substance, the alcohol and the free fatty acid are those defined below for the method according to the invention.

Composition

The invention also relates to a composition comprising hypophosphorous acid, and
organosulfonic acid,
said acids being in a ratio by mass of hypophosphorous acid to organosulfonic acid ranging from 0.01 to 0.4, preferably from 0.01 to 0.3, and more particularly from 0.01 to 0.25, and
optionally an aqueous diluent, organic, or hydroorganic, preferably water, and
optionally one or more additives.

The additives and the diluents are advantageously inert vis-à-vis the esterification reaction and preferably also vis-à-vis the subsequent transesterification reaction.

The diluent that can be used in the composition is advantageously chosen from oils, ethers, ketones, water or biodiesel. Mixtures of two or more of the above diluents may also be used.

The diluent cannot be an alcohol, an acid or an ester. This is because these compounds would not be inert vis-à-vis the esterification reaction.

Any additives present in the composition may also be of any type, and for example chosen from stabilisers, rheology modifiers, viscosity modifiers, flame retarders, surfactants, dyes, preservatives, corrosion inhibiters, odourisers, and others, as well as mixtures of two or more thereof.

A composition according to the invention that is particularly preferred comprises:
from 1% to 20% by weight hypophosphorous acid with respect to the total weight of hypophosphorous acid and sulfonic acid, and
from 80% to 99% by weight organosulfonic acid and derivatives thereof with respect to the total weight of hypophosphorous acid and organosulfonic acid.

According to a particular embodiment of the invention, the composition comprises from 5 to 20% by weight, preferably from 8 to 15% by weight with respect to the total weight of the hypophosphorous acid composition, from 30 to 70% by weight, preferably from 40 to 60% by weight with respect to the total weight of the methanesulfonic acid composition, said acids being situated in a ratio by mass of hypophosphorous acid to organosulfonic acid ranging from 0.01 to 0.4, preferably from 0.01 to 0.3, and more particularly from 0.01 to 0.25, and from 20 to 40% by weight with respect to the total weight of the water composition.

Method

Another object of the invention is a method for esterification of free fatty acids included in a fatty substance, comprising the following successive steps:

(a) providing a fatty substance comprising from 1% to 100% by weight at least one fatty acid;

(b) adding at least one alcohol;

(c) adding a composition as defined above, that is to say a composition comprising hypophosphorous acid, and organosulfonic acid, said acids being situated in a ratio by weight of hypophosphorous acid to organosulfonic acid ranging from 0.01 to 0.4, preferably from 0.01 to 0.3, and more particularly from 0.01 to 0.25, and optionally an aqueous diluent, organic, or hydroorganic, preferably water, and optionally one or more additives;

(d) conducting the esterification reaction at a temperature lying between ambient temperature and 150° C., preferably between 50° C. and 140° C., more preferentially between 60° C. and 130° C., at atmospheric pressure or under a vacuum ranging up to 1 kPa, preferably between 1 kPa and 100 kPa, preferably 1 kPa and 50 kPa, preferably from 5 kPa to 25 kPa.

The method according to the invention may comprise a supplementary step, after step (d): step (e) of recovering the organic phase comprising fatty acid esters.

The method according to the invention may comprise a step (e) of recovery of the organic phase comprising less than 10%, preferably less than 6%, preferably again less than 5%, better still less than 2% by weight free fatty acids.

According to one embodiment of the invention, elimination of the water contained in the alcohol is carried out, which may impair the subsequent transesterification reaction in a basic medium.

Thus the optional step (e) may take place after a step of separating the esterification alcohol and the water.

The separation of the esterification alcohol and the water is carried out in accordance with conventional techniques known to persons skilled in the art, such as distillation, settling, partial or total evaporation and/or optional addition of glycerol with sodium hydroxide added, and then separation of the phases by settling.

The fatty substance used as raw material at step a) may be any type known per se. This may be any type of oil or fat of vegetable or animal origin, as well as mixtures of said oils and fats, or a free fatty acid or a mixture of free fatty acids, optionally a mixture with one or more oils or fats of vegetable or animal origin.

Among the vegetable oils or fats, mention can be made, by way of non-limitative examples, of oils of sunflower, walnut, maize, soya, peanuts, colza, linseed, hemp, safflower, milk thistle, purslane, raspberry, blackcurrant, hazelnut, almond, wheat germ, borage, evening primrose (rose mallow) and poppy, stones, pips and seeds (for example apricot, almond, peach, cherry or plum stones, grape pips, marrow or pumpkin seeds, or cotton seeds), argan, palm, copra, sesame, olive, castor oil, coconut, Brazil nut. jatropha, babassu, karanja, neem, mahua, saijar, jojoba, tung, tall or tall oil, algae, as well as used frying oils (UFO) or used cooking oil (UCO), and others.

Among animal oils or fats, mention can be made, by way of non-limitative examples, of fish oils and fats, such as cod liver oil, whale oil, sperm whale, dolphin, seal, sardine, herring, sharks, oils and fats of bovines, pigs, goats, equidae and poultry, such as suet, lard, milk fat, bacon, and chicken, beef, pork and horse fats, and others.

The fatty substances described above generally comprise one or more so-called free fatty acids, by comparison with fatty acids in the form of esters with glycerol. Among the fatty acids encountered in the oils or fats used in the method of the invention, mention can be made, by way of non-limitative examples, of the free fatty acids chosen from carboxylic acids having 3 to 32 saturated or unsaturated carbon atoms, linear or branched, optionally including one or more rings. Preferably, the free fatty acids are chosen from carboxylic acids having from 6 to 32 carbon atoms, advantageously from 8 to 32 carbon atoms, in particular from 10 to 32 carbon atoms, highly preferably from 12 to 32 carbon atoms.

Preferably, the carboxylic acids chosen from propionic acid (3), butyric acid (4), caproic acid (6), caprylic acid (8), pelargonic acid (9), capric acid (10), undecanoic acid (11), lauric acid (12), myristic acid (14), myristoleic acid (14:1), palmitic acid (16), palmitoleic acid (16:1), margaric acid (17), stearic acid (18), oleic acid (18:1), ricinoleic acid (18:1), elaidic acid (18:1), petroselinic acid (18:1), vaccenic acid (18:1), linoleic acid (18:2), linolenic acids (18:3) and isomers thereof, licanic acid (18:3), arachidic acid (20), gadoleic acid (20:1), arachidonic acid (20:4), behenic acid (22) and erucic acid (C22:1), as well as mixtures of two or more thereof, in any proportions.

As indicated previously, the fatty substance used in the method of the invention comprises from 0.1% to 100%, preferably from 1% to 99%, preferably again from 3% to 95%, entirely preferably from 5% to 90% by weight at least one free fatty acid. The fatty substance may for example consist solely of a free fatty acid, or a mixture of free fatty acids, or comprise a mixture of at least one fatty acid with one or more vegetable or animal oils and/or fats.

An effective quantity of at least one alcohol is added to the fatty substance, for esterification of the fatty acids.

The alcohols that can be used can be chosen from monoalcohols, diols, alkyl triols, linear, branched or cyclic, preferably linear or branched, preferably again linear, comprising from 1 to 6 carbon atoms, preferably from 1 to 4 carbon atoms, and the mixtures of two or more thereof, in any proportions.

The alcohols that can be used can also be chosen from monoalcohols and polyols, preferably from alkyl monoalcohols and polyols, for example from alkyl monoalcohols, diols, triols and tetrols, linear, branched or cyclic, preferably linear or branched, preferably again linear, comprising from 1 to 6 carbon atoms, preferably from 1 to 5 carbon atoms, and mixtures of two or more thereof, in any proportions. For example, the alcohol can be chosen from methanol, ethanol, propanol, ethylene glycol, glycerol, pentaerythritol and mixtures thereof.

Preferably, the alcohol is chosen from methanol, ethanol, propanol, ethylene glycol and glycerol and mixtures thereof, and preferably the alcohol is methanol or glycerol.

The alcohol that is particularly preferred in the method of the invention is methanol.

Mixtures of two or more of the aforementioned alcohols can also be envisaged.

Advantageously, methanol and glycerol are the alcohols used in the method according to the invention.

Although it is possible to introduce, into the starting fatty substance, an equivalent molar quantity of alcohol with respect to the number of moles of fatty acids to be esterified, it is preferred to add a molar excess of alcohol. Thus the number of moles of alcohol can be between 1.1 and 50 times, preferably between 3 and 47 times, preferably again between 5 and 25 times, for example 10 times, the number of moles of fatty acids to be esterified. A quantity greater than 50 would not be profitable on economic level and with regard to the volumes to be treated. A stoichiometric quantity of alcohol could lead to an incomplete esterification of the free fatty acids.

Preferably, the molar ratio between the mixture of acids according to the invention: hypophosphorous acid and organosulfonic acid on the free fatty acids is between 0.001 and 10, preferably between 0.05 and 1.

The esterification reaction is conducted preferably under stirring at a temperature lying between ambient temperature and 150° C., preferably between 50° C. and 140° C., more preferentially between 60° C. and 130° C.

The reaction is conducted at atmospheric pressure or under vacuum ranging up to 1 kPa, preferably between 1 kPa and 100 kPa, preferably between 1 kPa and 50 kPa, preferably between 5 kPa and 25 kPa.

The esterification reaction is generally conducted for a period varying, according to the operating conditions, between a few tens of minutes and several hours. Normally, the reaction is carried out until the quantity of free fatty acids in the fatty substance loaded is less than 10% by weight, preferably less than 6% by weight, more particularly less than 5% by weight, even more advantageously less than 2% by weight.

As a general rule, according to the method of the present invention, a reaction period of between approximately 20 minutes and 5 hours is sufficient to obtain a conversion rate close to 100%.

After the esterification reaction, any excess of alcohol used for the esterification of the free fatty acids (such as methanol or glycerol) and water can be eliminated from the reaction medium in accordance with conventional separation methods, such as distillation, settling, or partial or total evaporation, two or more of these techniques being able to be combined with each other.

According to an alternative, the excess alcohol can be recycled in the esterification operation or in the transesterification operation, after having the water that it contains removed, in accordance with conventional techniques of elimination of water in alcohols. Furthermore, the catalyst can optionally be neutralised by adding a base such as potassium hydroxide, and then filtered after evaporation of the methanol-water phase.

At the end of the method, the reaction medium resulting from step d) may comprise a residual quantity of free fatty acids of less than 10% by weight, preferably less than 6% by weight, more particularly less than 5% by weight, even more advantageously less than 2% by weight, ideally less than 0.5% by weight, preferably less than 0.1% by weight.

The reaction medium may be subjected to various operations of neutralisation, washing or filtration, in order to obtain a mixture of fatty acid esters.

The advantage of this operation is being suited to any subsequent transesterification reaction.

According to another variant of the method according to the invention, the reaction medium resulting from step d) may be exchanged directly in another reaction, such as for example a transesterification reaction. In other words, the reaction medium resulting from step d) may be used as such, that is to say without any specific treatment. A monotopic method without separation of the reaction products can be envisaged.

Because of the low or even very low proportion of free fatty acids present in the reaction medium, the latter can be engaged in a method for preparing biodiesel, that is to say a transesterification reaction of fatty acid triglycerides, with an alcohol, preferably methanol. This transesterification reaction is generally carried out in the presence of a basic catalyst according to techniques now well known to persons skilled in the art.

It is in fact known that all oils or fats of vegetable or animal origin can be used for manufacturing biofuel, or more precisely biodiesel, as indicated above.

Biodiesel has very many advantages and among these mention can be made of its very low sulfur-product content, its very low aromatic-product content, its very rapid biodegradability compared with fuels of fossil origin, and its lubricating ability, which makes it possible to reduce premature wear in engines.

The preparation of biodiesel by transesterification, in the presence of a basic catalyst, is for example described in the patent applications WO 2006/043281 and US 2003/0167681. This method can be applied to animal and/or vegetable oils and fats that have undergone the previously described method of esterification of free fatty acids.

Another object of the invention is a method for preparing biodiesel using the composition as defined above, that is to say a composition comprising:
hypophosphorous acid and
organosulfonic acid,
said acids being in a ratio by mass of hypophosphorous acid to organosulfonic acid ranging from 0.01 to 0.4, preferably from 0.01 to 0.3, and more particularly from 0.01 to 0.25, and
optionally an organic or hydroorganic aqueous diluent, preferably water, and
optionally one or more additives.

Preferably, the method for preparing biodiesel according to the invention includes the method steps as defined above, that is to say the following successive steps:
(a) providing a fatty substance comprising from 1% to 100% by weight at least one fatty acid;
(b) adding at least one alcohol;
(c) adding a composition as defined above, that is to say a composition comprising
hypophosphorous acid, and
organosulfonic acid,
said acids being situated in a ratio by weight of hypophosphorous acid to organosulfonic acid ranging from 0.01 to 0.4, preferably from 0.01 to 0.3, and more particularly from 0.01 to 0.25, and
optionally an aqueous diluent, organic, or hydroorganic, preferably water, and
optionally one or more additives;
(d) conducting the esterification reaction at a temperature lying between ambient temperature and 150° C., preferably between 50° C. and 140° C., more preferentially between 60° C. and 130° C., at atmospheric pressure or under a vacuum ranging up to 1 kPa, preferably between 1 kPa and 100 kPa, preferably 1 kPa and 50 kPa, preferably from 5 kPa to 25 kPa.

More precisely, the untreated reaction medium obtained at the step (e) of the method for esterification of free fatty acids described above can be engaged in a method for preparing biodiesel comprising the following steps:

(f) optional filtration of the product of step (e);
(g) addition of a basic catalyst and at least one alcohol;
(h) conduct of the transesterification reaction at a temperature between 30° C. and 300° C., and at a pressure of between 10 kPa and 1000 kPa;
(i) recovery, and optionally drying and filtration, of the transesterified fatty acid esters.

It may be advantageous to purify the product straight from the esterification reaction of free fatty acids, in order to eliminate any species that may interfere with the subsequent transesterification reaction. Thus, it is possible to carry out a filtration, in accordance with conventional techniques known to persons skilled in the art, but also distillation, drying and other known techniques of refining untreated reaction products.

The basic catalyst is known per se and can advantageously be chosen from basic catalysts normally used in this field, that is to say from sodium hydroxide, potassium hydroxide, sodium methylate, potassium methylate, sodium carbonate, potassium carbonate, calcium carbonate and others. The basic catalyst may be supported, on resins, zeolites or metallic oxides (alumina, silica, zirconia, etc.). According to another aspect, the transesterification reaction may be conducted in the absence of a basic catalyst.

The alcohol or the mixtures of alcohols that can be used are generally chosen from alkyl monoalcohols, for example methanol, ethanol, propanol and butanol. The quantity of alcohol or alcohols introduced is advantageously such that the reaction medium comprises a molar excess of alcohol or alcohols with respect to the number of moles of esters, in order to favour the transesterification reaction.

The untreated transesterification reaction product mainly contains fatty acid esters (biodiesel) and glycerol, which is separated in accordance with conventional techniques. The fatty acid esters may finally optionally be dried, purified and filtered in accordance with conventional techniques in order to be able to be used as biofuels.

The following examples illustrate the present invention without however limiting the scope thereof. In these examples, the parts and the percentages are expressed by weight, unless indicated otherwise.

Examples

The following experiments were carried out:

1. Comparative Esterifications Denoted Reactions A to C

A 500 ml double-jacket reactor closed by a cap including six outlets is equipped with a thermometric probe, mechanical stirring, a septum that can be replaced at the start of manipulation by a pouring funnel for adding catalysts, a glass rod holding test pieces with three 316L stainless steel test pieces and a plunger tube with diffuser. On the last neck, there is a 15 cm straight refrigerator cooled to 10° C. followed by a swan neck with an air outlet, and then a graduated decanting bulb (5 ml, 10 ml, 15 ml). The air outlet at the end of the refrigerant is connected to a gas trap and then to the vacuum pump.

First, the dimensions and masses of the three stainless-steel test pieces are measured. The stainless steel is 316L stainless steel with a density of 7.99 g/cm³.

The reactor is preheated to 60° C. 226 g of oil at 93.5% free fatty acid, hereinafter denoted FFA, is introduced rapidly into the hot reactor (60° C.). Slow stirring (120 rpm) is applied. 81 g of glycerol is then added to the oil in the reactor. When the addition of the glycerol is finished, the stirring is increased to 500 rpm. The reactor is put under nitrogen with degassing of the medium by means of a plunger tube. The temperature is increased from 60 to 130° C. over approximately 30 minutes. As from 120° C., the inerting is left for 15 minutes.

The acid or acids are then added by means of a needle through the septum.

The three comparative esterification reactions denoted A, B and C are carried out with various acids appearing in the following table:

| | Acids |
|---|---|
| A | 0.5% AMS alone, i.e. 1.11 g of 70% AMS, i.e. 0.5% with respect to the oil |
| B | 0.5% $H_2SO_4$ alone, i.e. 1.11 g of 96% $H_2SO_4$, i.e. 0.5% with respect to the oil |
| C | a mixture of 0.07% $H_3PO_2$ and 0.5% $H_2SO_4$. i.e. 0.16 g of 50% hypophosphorous acid, i.e. 0.07% with respect to the oil, and 1.1 g of 96% $H_2SO_4$, i.e. 0.5% with respect to the oil |

The reactor is then put under a vacuum of 1 kPa and the reaction medium is stirred for 6.5 hours at 130° C. At the end of the reaction, the medium is cooled to 40° C. and then put under air and settled in a settling bulb: the organic phase is situated at the top and the aqueous phase containing the glycerol is situated at the bottom. 263 g of organic phase is obtained.

The three 316L stainless steel test pieces are immersed in ultrapure water and then washed with ethanol, and then dried in air and weighed.

2. Esterification According to the Invention Denoted Reaction D

The operating mode described above is followed. Following the step of mixing the reagents, 1.11 g of 70% AMS, i.e. 0.5% with respect to the oil, with 0.16 g of 50% hypophosphorous acid added, i.e. 0.07% with respect to the oil, i.e. a ratio by mass of $H_3PO_2$ expressed as anhydrous equivalent to 70% AMS of 0.08/0.77=0.1, is then added by means of a needle through the septum. The reactor is then put under a 1 kPa vacuum and the reaction medium is stirred for 6.5 hours at 130° C. At the end of the reaction, the medium is cooled to 40° C. and then put under air and settled in a settling bulb: the organic phase is situated at the top and the aqueous phase containing the glycerol is situated at the bottom. 263 g of organic phase is obtained.

The three 316L stainless steel test pieces are immersed in ultrapure water and then washed with ethanol, and then dried in air and weighed.

3. Results

For each method followed, the loss of mass of the stainless steel test pieces present in the reactor is calculated. This loss of mass makes it possible to calculate the rate of corrosion in μm/year in accordance with the following formula:

$$V=[\Delta p/(d \times S \times 10^{-4} \times t)] \times 365$$

with V=rate of corrosion expressed in μm/year
Δp=loss of mass of the test piece tested expressed in g,
d=density of the material of the test piece tested expressed in g/cm³
S=surface area of the test piece tested expressed in cm²
t=duration of the manipulation expressed in days The following table summarises the results obtained for the comparative esterification reactions and with the mixture according to the invention.

|   | Acids | Corrosion rate (μm/year) | Conversion (%) |
|---|---|---|---|
| A Comparative | AMS | 585 | >95 |
| B Comparative | $H_2SO_4$ | 900 | >95 |
| C Comparative | $H_3PO_2 + H_2SO_4$ | 515 | 87 |
| D Invention | $H_3PO_2$ + AMS | 35 | >95 |

The results show very clearly that the combination of the two acids as claimed, namely hypophosphorous acid and methanesulfonic acid, leads to a very great reduction in corrosion, while leading to a very high conversion rate.

The invention claimed is:

1. A corrosion inhibiter capable of esterifying free fatty acids and comprising hypophosphorous acid and an organosulfonic acid, wherein the organosulfonic acid is of formula R—$SO_3H$, wherein R is a saturated linear or branched hydrocarbon chain containing 1 to 4 carbon atoms.

2. The corrosion inhibitor according to claim 1, wherein the organosulfonic acid is methanesulfonic acid.

3. A composition comprising
hypophosphorous acid, and
an organosulfonic acid, wherein the organosulfonic acid is of formula R—$SO_3H$, wherein R a saturated linear or branched hydrocarbon chain containing 1 to 4 carbon atoms,
the hypophosphorous and organosulfonic acids being in a ratio by mass of hypophosphorous acid to organosulfonic acid ranging from 0.01 to 0.4, and
optionally an aqueous, organic or hydroorganic diluent, and
optionally one or more additives.

4. The composition according to claim 3, comprising:
from 1% to 20% by weight of the hypophosphorous acid with respect to the total weight of hypophosphorous acid and organosulfonic acid, and
from 80% to 99% by weight of the organosulfonic acid and derivatives thereof with respect to the total weight of hypophosphorous acid and organosulfonic acid.

5. A method for the esterification of fatty acids, comprising the following successive steps:
(a) providing a fatty substance comprising from 1% to 95% by weight of at least one free fatty acid;
(b) adding at least one alcohol;
(c) adding a composition comprising
hypophosphorous acid, and
organosulfonic acid,
the hypophosphorous and organosulfonic acids being in a ratio by mass of hypophosphorous acid to organosulfonic acid ranging from 0.01 to 0.4, and
optionally an aqueous, organic or hydroorganic diluent, and
optionally one or more additives;
(d) conducting the esterification reaction at a temperature between ambient temperature and 150° C. and at atmospheric pressure or under a vacuum ranging up to 1 kPa.

6. The method according to claim 5, including after step (d), the following step:
(e) recovering the organic phase comprising fatty acid esters.

7. The method according to claim 5, wherein the fatty substance is an oil or a fat of vegetable or animal origin, or a used frying oil, or a mixture of the aforementioned oils or fats, optionally a mixture with one or more oils or fats of vegetable or animal origin.

8. The method according to claim 5, wherein the fatty substance is chosen from oils of sunflower, walnut, maize, soya, peanuts, colza, linseed, hemp, safflower, milk thistle, purslane, raspberry, blackcurrant, hazelnut, almond, wheat germ, borage, evening primrose (rose mallow) and poppy, stones, pips and seeds, of argan, palm, copra, sesame, olive, castor oil, coconut, Brazil nut, jatropha, babassu, karanja, neem, mahua, saijar, jojoba, tung, tall or tall oil, algae, used frying oils, fish fat oils, oils and fats of bovines, pigs, goats, equidae and poultry, as well as mixtures of two or more thereof.

9. The method according to claim 5, wherein the fatty substance comprises from 3% to 95% by weight of at least one free fatty acid.

10. The method according to claim 5, wherein the free fatty acids are chosen from saturated or unsaturated, linear or branched carboxylic acids having from 3 to 32 carbon atoms, optionally including one or more rings.

11. The method according to claim 5, wherein the alcohol is chosen from linear, branched or cyclic monoalcohols, diols or alkyl triols, comprising from 1 to 6 carbon atoms, and mixtures of two or more thereof, in any proportions.

12. The method according to claim 11, wherein the alcohol is chosen from methanol, ethanol, propanol, ethylene glycol, and glycerol and mixtures thereof.

13. A method for preparing biodiesel, comprising the steps as defined in claim 5.

* * * * *